United States Patent
Logier et al.

(10) Patent No.: US 10,166,139 B2
(45) Date of Patent: Jan. 1, 2019

(54) DEVICE ENABLING FLOW OF FOOD BOLUS BETWEEN TWO STOMAS

(71) Applicant: CENTRE HOSPITALIER REGIONAL UNIVERSITAIRE DE LILLE, Lille (FR)

(72) Inventors: Régis Logier, Marquette lex Lille (FR); Jean-Pierre Sozanski, Villeneuve d'Ascq (FR); Jean-Robert Nzamushe Lepan Mabla, Braines l'Alleud (FR)

(73) Assignee: CENTRE HOSPITALIER REGIONAL UNIVERSITAIRE DE LILLE (FR)

( * ) Notice: Subject to any disclaimer, the term of this patent is extended or adjusted under 35 U.S.C. 154(b) by 660 days.

(21) Appl. No.: 14/759,885

(22) PCT Filed: Jan. 27, 2014

(86) PCT No.: PCT/FR2014/050148
§ 371 (c)(1),
(2) Date: Jul. 8, 2015

(87) PCT Pub. No.: WO2014/122378
PCT Pub. Date: Aug. 14, 2014

(65) Prior Publication Data
US 2015/0351954 A1    Dec. 10, 2015

(30) Foreign Application Priority Data

Feb. 5, 2013   (FR) ..................................... 13 00229

(51) Int. Cl.
*A61F 5/445*   (2006.01)
*A61M 1/00*   (2006.01)
(Continued)

(52) U.S. Cl.
CPC ............ *A61F 5/445* (2013.01); *A61F 5/4405* (2013.01); *A61M 1/00* (2013.01); *A61M 1/0066* (2013.01);
(Continued)

(58) Field of Classification Search
CPC combination set(s) only.
See application file for complete search history.

(56) References Cited

U.S. PATENT DOCUMENTS 3,750,194 A  *  8/1973  Summers ................ A61F 2/004
                                                    128/DIG. 25
3,828,782 A  *  8/1974  Polin ...................... A61F 5/445
                                                    604/103.03
(Continued)

FOREIGN PATENT DOCUMENTS

WO    WO 2009/046997 A2    4/2009
WO    WO 2009046997 A2  *  4/2009  ............... A61B 5/03

OTHER PUBLICATIONS

International Search Report dated May 6, 2014 issued in corresponding International patent application No. PCT/FR2014/050148.

*Primary Examiner* — Philip R Wiest
*Assistant Examiner* — Guy K Townsend
(74) *Attorney, Agent, or Firm* — Ostrolenk Faber LLP (57) ABSTRACT

A device enabling food bolus flow between two stomas, said device having a pump forming means (3), said pump forming means (3) having an entry opening and an exit opening and being suitable for sucking food bolus through said entry opening and releasing it through said exit opening. The device further includes: —first watertight connection means (11) suitable for connecting said entry opening to a upstream stoma (S1) located on a patient's abdominal wall; —second watertight connection means (1) suitable for connecting said exit opening to a downstream stoma (S2), located on said patient's abdominal wall; said pump forming means being
(Continued)

able to be activated by a user and suitable for being mounted on a patient's body, particularly on said patient's abdomen, in such a manner that once said device is mounted onto said patient's abdomen, food bolus flow can circulate from said upstream stoma (S1) to said downstream stoma (S2) outside of said patient's abdomen.

18 Claims, 6 Drawing Sheets

(51) Int. Cl.
    *A61F 5/44*         (2006.01)
    *A61M 39/10*      (2006.01)

(52) U.S. Cl.
    CPC ....... *A61M 39/10* (2013.01); *A61M 2205/106* (2013.01); *A61M 2205/3303* (2013.01); *A61M 2210/106* (2013.01); *A61M 2210/1064* (2013.01)

(56) References Cited

U.S. PATENT DOCUMENTS

| | | | | |
|---|---|---|---|---|
| 4,222,377 | A * | 9/1980 | Burton | A61F 2/004 128/DIG. 25 |
| 5,261,898 | A * | 11/1993 | Polin | A61F 2/0013 604/327 |
| 5,454,389 | A * | 10/1995 | Hubbard | A61F 5/445 134/104.4 |
| 5,484,402 | A * | 1/1996 | Saravia | A61M 1/0043 604/249 |
| 5,593,443 | A * | 1/1997 | Carter | A61F 2/004 128/DIG. 25 |
| 5,738,661 | A * | 4/1998 | Larice | A61F 5/442 604/180 |
| 5,807,313 | A * | 9/1998 | Delk | A61M 1/0064 604/151 |
| 6,001,086 | A * | 12/1999 | Rammacher | A61F 5/44 604/327 |
| 6,402,767 | B1 * | 6/2002 | Nash | A61B 17/11 606/153 |
| 6,551,235 | B2 * | 4/2003 | Forsell | A61F 2/004 600/30 |
| 6,752,754 | B1 * | 6/2004 | Feng | A61F 2/0036 600/30 |
| 6,840,923 | B1 * | 1/2005 | Lapcevic | A61F 5/442 604/19 |
| 7,799,074 | B2 * | 9/2010 | Grimme | A61M 1/1081 418/61.3 |
| 8,075,539 | B2 * | 12/2011 | Nishtala | A61M 39/10 604/328 |
| 9,155,623 | B2 * | 10/2015 | Forsell | A61B 17/1666 |
| 2001/0023337 | A1 | 9/2001 | Lapcevic | |
| 2002/0091365 | A1 * | 7/2002 | McNally | A61J 15/0015 604/332 |
| 2004/0039348 | A1 * | 2/2004 | Kim | A61M 3/0241 604/264 |
| 2004/0078012 | A1 * | 4/2004 | Uno | A61F 2/04 604/317 |
| 2004/0098113 | A1 * | 5/2004 | Forsell | A61F 2/0036 623/1.25 |
| 2004/0122527 | A1 * | 6/2004 | Imran | A61F 2/04 623/23.67 |
| 2004/0220516 | A1 | 11/2004 | Solomon et al. | |
| 2005/0187578 | A1 * | 8/2005 | Rosenberg | A61M 25/04 606/232 |
| 2005/0216042 | A1 * | 9/2005 | Gertner | A61B 17/0401 606/151 |
| 2008/0039809 | A1 | 2/2008 | Kamen et al. | |
| 2010/0217213 | A1 * | 8/2010 | Forsell | A61F 5/4404 604/319 |
| 2011/0066254 | A1 * | 3/2011 | Forsell | A61M 1/1068 623/23.64 |
| 2012/0123379 | A1 * | 5/2012 | Forsell | A61F 5/445 604/385.03 |
| 2013/0231523 | A1 * | 9/2013 | Forsell | A61F 2/0036 600/30 |
| 2015/0351954 | A1 * | 12/2015 | Logier | A61M 1/00 604/335 |
| 2015/0367111 | A1 * | 12/2015 | Kane | A61J 15/0049 604/9 |

* cited by examiner

DEVICE ENABLING FLOW OF FOOD BOLUS BETWEEN TWO STOMAS

CROSS REFERENCE TO RELATED APPLICATIONS

The present application is a 35 U.S.C. § 371 National Phase conversion of PCT/FR2014/050148, filed Jan. 27, 2014, which claims benefit of French Application No. 1300229, filed Feb. 5, 2013, the disclosure of which is incorporated herein by reference. The PCT International Application was published in the French language.

TECHNICAL FIELD OF THE INVENTION

The present invention concerns a device enabling flow of food bolus between two stomas.

BACKGROUND OF THE INVENTION

In order to treat diseases such as acute diverticulitis, rectal cancer, intestinal injuries and inflammatory bowel diseases it is often necessary to remove part of the bowel and create stomas. To do this, the ends of the bowel formed by removal of a part of bowel are sutured to the patient's abdominal skin. The two ends are sutured open in order that the inside of the bowel is accessible in the patient's abdomen. In the sense of this invention, the stoma represents the open end of the bowel which is flush with the patient's abdominal skin. This treatment approach may be temporary or permanent and causes many restrictions in terms of quality of life and functioning of the digestive system.

In colostomies (stomas of the colon) and ileostomies (stomas of the small bowel), normal intestinal function is interrupted and food bolus crosses the abdominal wall through the stoma. Food bolus then fills a stoma bag which needs to be emptied regularly. Although every effort is made to maintain the integrity of the bowel and tissues and to treat and reduce patients' pain and discomfort, in many cases the stoma causes increased patient distress and suffering. In addition, some patients with ileostomies require parenteral nutrition (i.e. by the intravenous route) because of the inadequate absorption of oral nutrients as a result of food bolus passing an insufficient length of bowel. Long term parenteral nutrition may be associated with side effects including infectious complications and/or liver disturbances. In addition it requires long term hospital or at home hospitalization resulting in high costs. In addition, patients' quality of life is reduced leading to a sedentary lifestyle and repeated stoma care.

Once no risk of infection of the peritoneum remains the two parts of the bowel are reconnected to each other; the downstream part through which food bolus did not pass throughout the time when bowel transit was interrupted will have degenerated, complicating full convalescence and a return of normal bowel transit allowing normal nutrient absorption.

Under these circumstances it is important to identify effective means of improving the quality of life of patients with stomas.

Document WO 2009/046997A2 describes a device for circulating food bolus intended to be implanted into the patient's body in order to enable the bolus to leave the body through a stoma, or to circulate between two portions of bowel connected by the device, implanted into the patient's body. This type of device causes problems with infection if food bolus leaks into the patient's body. Implantation of the device requires a surgical procedure which is not without danger in a patient who is already weakened by a disease.

SUMMARY OF THE INVENTION

One aim of the invention is to propose a new device which can help to improve quality of life of patients who have undergone surgery and in whom stomas have been created during said surgical procedure.

To do this, the present invention proposes a device enabling food bolus flow between two stomas, said device comprising pump forming means, said pump forming means having an entry opening and an exit opening and being suitable for sucking food bolus through said entry opening and releasing it through said exit opening. According to the present invention, characteristically, the device further comprises first watertight connection means, suitable for connecting said entry opening to a upstream stoma located on a patient's abdominal wall second watertight connection means suitable for connecting said exit opening to a downstream stoma located on said patient's abdominal wall; said pump forming means being able to be activated by a user and suitable for being mounted on a patient's body, particularly on said patient's abdomen, in such a manner that once said device is mounted onto said patient's abdomen, food bolus flow can circulate from said upstream stoma to said downstream stoma outside of said patient's abdomen.

Circulation of food bolus throughout the patient's whole intestines can preserve the full functionality of the portion of the intestine located downstream to the stomas. In time, any parenteral nutrition can be stopped because of better nutrient absorption. As the device of the invention is portable, it does not impede patient's movements.

In the context of this invention, the terms "food bolus" refer to the intestinal food bolus, i.e. food bolus contained within the patient's intestines.

Positioning or mounting the invention device does not require a surgical procedure and uses the stomas which have been created by surgery. The use of the invention device involves no risk of infection, as food bolus circulates outside of the patient's body when it is not circulating within a portion of intestine. The sites of possible leakage are therefore located outside of the patient's body.

The pump forming means may for example be fixed onto a belt, a shoulder strap, a combination of both of these, a pair of slings or onto any other item which can be carried by a patient, user or attached to his/her body. They are therefore suitable for being assembled onto a patient's body.

According to a particular embodiment, said first watertight connection means and/or said second watertight connection means comprise a base onto which a food bolus collector is mounted, said base having a first surface adapted for being fixed in a watertight manner to a patient's skin, said base further having a second surface comprising means for mounting said connector and at least one passage provided within said base and opening into said collector.

The base may for example be affixed to the patient's skin. The fixation method for the base onto the patient's abdominal skin is not limited according to the present invention. The passage provided within the base is intended to be positioned next to a stoma. In addition, when the first and second watertight connection means are separate, and each arranged on a single stoma, each only contains one passage opening into the collector.

Advantageously, said second watertight connection means comprise an exit flow tube connected to said exit opening and fashioned in order to be introduced into a patient's intestine through said downstream stoma. This enables to avoid any leakage or reflux towards the downstream stoma. When the second watertight connection means comprise a base provided with a passage, the exit flow tube runs through said passage and extends beyond the base in the opposite direction to the collector.

A cannula called a Pezzer cannula may be advantageously used as the exit flow tube.

According to another specific embodiment of the watertight connection means, said first watertight connection means and said second watertight connection means comprise a common base and a common connector. This particular embodiment is well suited to stomas described as close, which are positioned next to each other. In this case, the base comprises two passages which are provided in order to be each next to a stoma.

The pump forming means are not limited according to the invention. According to a particular embodiment of the pump forming means, said pump forming means comprise at least one deformable part and means for deforming said deformable part, said deformable part defining at least partially a space communicating with said communicating with said first watertight connection means through said entry opening and communicating with said second watertight connection means through said exit opening, deformation of said deformable part changes the volume of said space, with the result that said volume of said space is reduced and food bolus inside said space is expressed into said second watertight connection means, and when the volume of said space increases, food bolus coming from said first watertight connection means is sucked into said space.

According to one embodiment, said deformable part is a membrane and said pump forming means comprise a casing, the internal space of which is divided into a first and second chamber by said membrane, said first chamber communicating with said first watertight connection means and said second watertight connection means, said pump forming means further comprising means for sucking/releasing a fluid, which are connected to said second chamber and which are capable of varying the pressure of said fluid within said second chamber, with the result that said means for sucking/releasing a fluid vary the curve of said deformable membrane, therefore enabling the volume of the first chamber to change and food bolus to be sucked into said first chamber or released from said first chamber.

Advantageously, the device comprises first valve forming means provided for avoiding reflux of food bolus sucked by said pump forming means towards said first watertight connection means and/or second valve forming means provided for avoiding reflux of food bolus released by said pump forming means towards said second watertight connection means.

The first and second valve forming means are not limited according to the invention. They may include any type of existing valve, duckbill type, or other.

The pump forming means may be activated through a switch located on the pump forming means or through a switch suitable for being mounted onto the patient's body.

Advantageously, the device comprises control means for controlling the pump forming means; said control means are separate from said pump forming means. These control means may be detached from the patient's body and activated remotely (by IR or other). The control means may be a remote control specially dedicated to the pump forming means of the invention device. It may also be a tablet, mobile phone or any other programmable item able to interface with the pump forming means.

Advantageously, the device comprises control means for said pump forming means, said control means comprising an internal real time clock suitable for activating said pump forming means after a given rest period, said rest period being selected by the user, and means of programming said real time internal clock which allow said rest period to be selected.

The automatic action of pumping at the end of said rest period also enables transit to be started in the part of the intestine located upstream to the stoma.

According to one embodiment of said control means, said control means further comprise:
  detection means for detecting the presence of food bolus downstream to said first watertight connection means and/or upstream to said second watertight connection means, said detection means being able to measure a parameter depending on food bolus presence or absence and to activate said pump forming means once the value of said parameter corresponds to the presence of food bolus in said device;
  means for triggering said detection means, which activate said detection means after a test period selected by the user; and
  means for adjusting said test period.

Said detection means may, for example, comprise at least one sensor selected from capacitive sensors, optical sensors, temperature sensors and pressure sensors.

Advantageously, said control means further comprise means for automatically triggering said pump forming means at the end of a safety period which can be set by the patient/user. The invention device may therefore be used in the event of failure of the detection means without specific intervention from the patient.

The invention also concerns a method for circulating food bolus between an upstream stoma created in a patient's abdomen and a downstream stoma. According to said method, food bolus contained in the patient's intestine linked to said upstream stoma is sucked upstream to said upstream stoma and then released into said patient's intestine through said downstream stoma and downstream to said downstream stoma. This method may be used to improve patient feeding, contributing to the patient's convalescence after stomas surgery. This method helps to reduce the length of the period during which the patient has a stoma, this period preceding the possible operation designed to reconnect the two portions of intestine.

Advantageously, the presence of food bolus is detected in upstream stoma or between said upstream stoma and said downstream stoma before sucking food bolus contained in the intestine upstream to said upstream stoma.

This invention also concerns a computer programme product comprising instructions which, once they are implemented on a calculator linked to the invention activates one of the methods for circulating food bolus as described above.

BRIEF DESCRIPTION OF THE DRAWINGS

This invention, its characteristics and the different benefits which it provides will appear more clearly on reading the detailed descriptions of two embodiments described below, which are given as explanatory and non-exhaustive examples, referring to the annexed figures on which.

DESCRIPTION OF PREFERRED EMBODIMENTS

Figure 1:
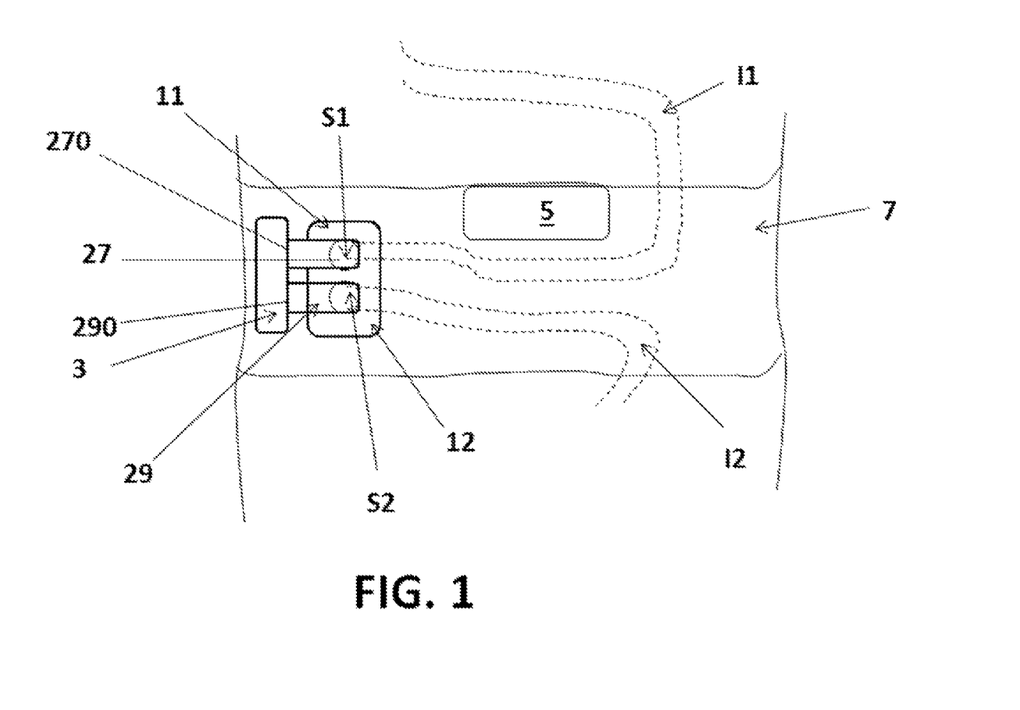
FIG. 1 represents schematic view of a first embodiment the invention, assembled onto the abdomen of a patient with two close stomas.

With reference to FIG. 1, the patient's abdomen has an upstream stoma S1 and a downstream stoma S2. These two stomas are adjacent to each other and are called close stomas. Depending on the type of surgery, the stomas may also be further apart and for example each positioned on a patient's flank. The upstream stoma S1 communicates with the upstream portion I1 of the intestine which follows on from the stomach (not shown). The downstream stoma S2 communicates with the downstream portion of the intestine I2 which continues on to the anus (not shown). The two portions I1 and I2 of the intestine are shown in dotted lines.

In FIG. 1, first watertight connection means 11 are assembled onto the upstream stoma S1 whereas second watertight connection means 12 are assembled onto the downstream stoma S2. First and second watertight connection means 11 and 12 are connected to the pump forming means 3 which are controlled by control means 5. First watertight connection means 11 are connected to pump forming means 3 through a sucking passage or sucking channel 27 which opens into pump forming means 3 through an entry opening 270. Second watertight connection means 12 are connected to pump forming means 3 through a releasing passage 29. The releasing passage 29 (or release channel) opens into pump forming means 3 through an exit opening 290. First and second watertight connection means 11 and 12 and pump forming means 3 are mounted onto a belt 7 provided around patient's abdomen. The invention device is therefore portable and in no way impedes the patient's mobility. Control means 5 as shown in FIG. 1 are also mounted onto the belt 7. They may, nevertheless, according to the invention, be disconnected from the belt or entirely separate from the belt. They may for example comprise an existing touch screen tablet which runs on a specific computer program product.

Figure 2:
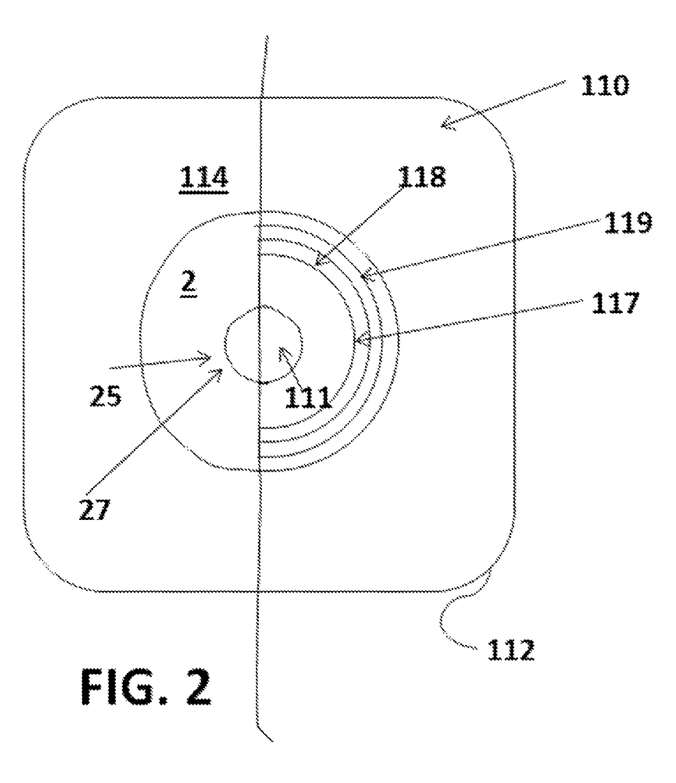
FIG. 2 represents a schematic elevated view of a specific embodiment the first watertight connection means, with a partial horizontal section.

With reference to FIG. 2, a particular embodiment of the first watertight connection means 11 will now be described. The first watertight connection means 11 comprise a base 110 which is a flexible sheet. This base 110 has a lower surface 112 which is coated with special glue enabling the base to be fixed to a patient's skin. The superior surface 114 of the base 110 comprises a fixing part 117 which is provided on the base 110. This fixing part 117 comprises a ring 119 almost perpendicular to the base 110, said base being almost flat. The ring 119 is surrounded by a watertight throat 118. The ring 119 and watertight throat 118 surround a passage 111 created in the base 110. The fixing part 117 surrounds the passage 111. The passage 111 is surrounded by the throat 118 which itself is surrounded by the ring 119. When the first watertight connection means 11 are assembled onto the patient's abdomen, the passage 111 is located at the level of the upstream stoma S1 in order to enable food bolus to pass through the passage 111.

As shown on FIG. 2, first watertight connection means 11 also comprise a collector 2. The collector 2 is a box which is suitable for being assembled in a watertight manner onto the fixing part 117 and which has an opening suitable for being connected to an exit flow tube as explained below.

The second watertight connection means 12 can be identical to the first means 11 described above with the exception of the sucking passage 27 which is replaced by the release passage 29 connected to the releasing opening of the pump forming means.

Figure 3:
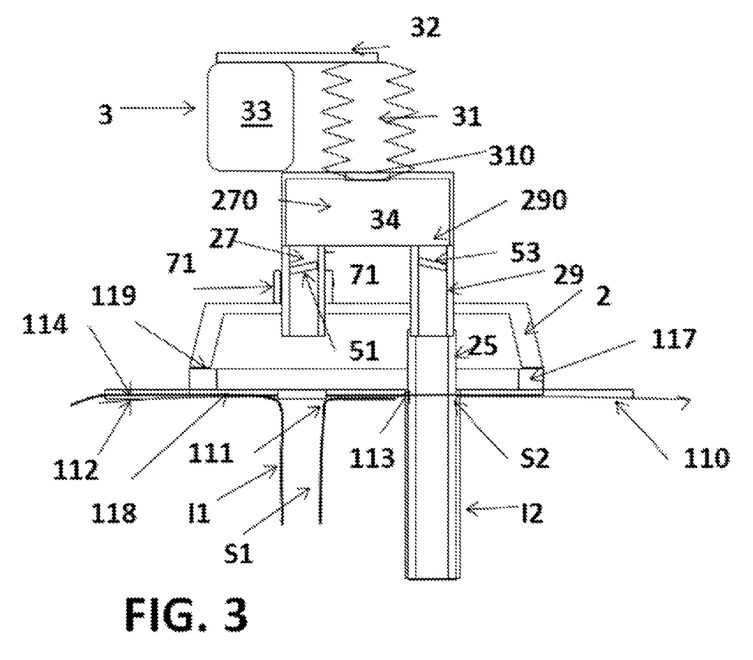
FIG. 3 represents a schematic view according to a partial transverse plane of an alternative embodiment of the first embodiment.

With reference to FIG. 3, an alternative embodiment will now be described. In this specific alternative embodiment, first connection means 11 and second connection means 12 comprise a single base 110 and a single collector 2. The base 110 comprises a first passage 111 and a second passage 113 which are arranged side by side. The base 110 is glued to the patient's abdomen. The first passage 111 is located next to the upstream stoma S1 whereas the second passage 113 is located next to the downstream stoma S2. The collector 2 is mounted onto the base 110 using the fixing part 117. The sucking passage 27 opens into the collector 2 almost immediately above the upstream stoma S1. The other end of the sucking passage 27 opens into a connecting passage 34 through the entry opening 270. The collector 2 also comprises a second opening through which the release passage 29 passes through. The release passage 29 is located above the downstream stoma S2. The release passage 29 also opens into said connection passage 34 through an exit opening 290. The other end of the release passage 29 is located in the collector 2 above the downstream stoma S2 and is connected to an exit flow tube 25. Said exit flow tube extends through the second passage 113 and beyond the base 110. In FIG. 3, the exit flow tube 25 extends into the downstream portion I2 of the intestine downstream to the downstream stoma S2. With reference to FIG. 3, the pump forming means 3 comprise a bellows system 31 activated through a motor 33 via an arm 32. The motor 33 in this case is a linear motor. A connecting crankshaft system combined with a rotatory motor may also be used. The bellows 31 contain an opening 310 which opens into the connection passage 34 between the entry opening 270 and the exit opening 290. The sucking passage 27 is equipped with an anti-reflux valve 51 duckbill type for example, in order to avoid any reflux of food bolus sucked into the connecting passage 27 towards the collector 2. Similarly the release passage 29 is equipped with an anti-reflux valve 53 duckbill type, in order to avoid any reflux of food bolus located inside the exit flow tube 25 towards the connection passage 34.

The sucking passage 27 is equipped with means for detecting the presence of a food bolus upstream to the pump forming means 3, between its output from collector 2 and the entry opening 270. These means comprise a capacitive sensor 71 which can measure the permittivity of the medium contained in the sucking passage 27. The capacitive sensor 71 is formed from two plates of dimensions in the region of 15 mm by 10 mm positioned around the sucking passage 27.

This capacitive sensor 71 may be replaced by a light sensor formed from an LED diode in the IR or visible range and a photodiode positioned next to the LED, the sucking passage 27 separating the LED from the photodiode. The photodiode response is quasi-proportional to the light intensity emitted by the LED. Therefore, when food bolus is present within the sucking passage 27, the photodiode response falls because of absorption of the light emitted by the LED by food bolus.

A temperature sensor may also be used, a rise in temperature in the sucking passage indicating the presence of the food bolus.

The release passage 29 (or exit flow passage) may also be equipped with a sensor chosen from amongst the various types of sensors described above in addition to the sensor equipping the sucking passage 27 or as a replacement for this sensor.

Control means 5 comprise, according to one embodiment, a microcontroller linked to specific software dedicated for the management of the different sensors and controlling the motor 33 for the pump forming means 3. They also comprise an LCD display module, a function touch screen interface and signalling LED, a non-volatile memory for storage of information throughout the entire care period (several weeks), measurements for processing sensor signals, a Bluetooth® module for remote reading and writing of information from the sensor measurements and specific programming according to patient requirements.

The functioning of this first embodiment will be described with reference to FIGS. 1 and 3.

First, the device is calibrated before operation. The sensor 71 measures the capacitive of the air filling the sucking passage 27. This represents the reference value for the "empty" device, i.e. when it does not contain food bolus.

The sensor 71 then regularly measures the capacitive of the medium contained in the sucking passage 27. The time between two capacitive measurements is a test period which is adjustable by the user using the control means 5. When some food bolus arrives through the upstream stoma S1 as a result of contractions of the upstream portion I1 of the intestine (or pumped by the pump forming means 3), food bolus enters the collector 2 and then enters the section of the sucking passage 27 located near the sensor 71. The sensor 71 performs its measurements regularly, consecutive measurements being separated by the test period. One of these measurements is recorded when food bolus is inside the sucking passage 27. The sensor 71 measures the capacitive of the medium filling the sucking passage 27, compares it with the reference value and detects the presence of the food bolus. It then activates the pump forming means 3. The motor 33 then compresses the bellows system 31 and then releases it, thereby sucking food bolus from the collector 2 into the bellows system 31 through the opening 310. When the bellows system 31 is open, it contains food bolus. The motor 33 then recompresses the bellows system 31 and food bolus is then expressed into the connection passage 34 and passes through the exit flow tube 25. Food bolus is thereby injected into the downstream portion I2 of the intestine.

Detection means for detecting the presence or not of food bolus may comprise two sensors which each measure a different parameter. If the two sensors indicate the presence of the food bolus, they start the pump forming means 3 sucking food bolus contained in the sucking passage.

Preferably, the device also comprises safety triggering means which routinely activates the pump forming means after a safety period which is adjustable by the user through the control means.

A second embodiment will now be described, referring to FIGS. 4 to 6. The parts in common with the first embodiment are referenced identically.

Figure 4:
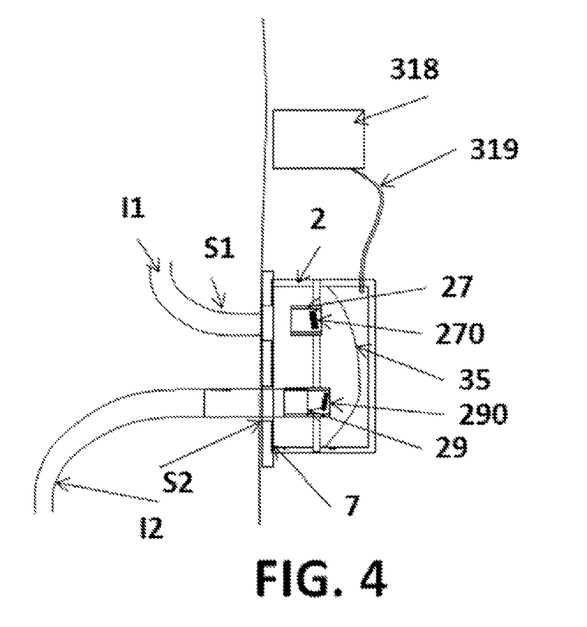
FIG. 4 represents schematic view according to a vertical section of a second embodiment the invention mounted onto a patient.

With reference to FIG. 4, the device according to the invention comprises first watertight connection means 11, which also forms second watertight connection means. In FIG. 4, first watertight connection means 11 are assembled onto the patient's abdomen in the same way as described for the first embodiment. The belt 5 carries an air pump 318 and control means 5. A membrane pump contained in a casing 35 is assembled over the collector 2 and will be described in more detail with reference to FIG. 5. The membrane pump is connected to the air pump 318 by the connection tube 319.

In this second embodiment, the first and second watertight connection means comprise the same base 110 and the same collector 2. As shown on FIG. 5, a casing 35 is assembled over the connector 2. The casing 35 forms a watertight cavity above the collector 2. The casing 35 comprises a deformable membrane 351 which separates the cavity into two chambers, i.e. a first chamber 320 for receiving food bolus, and a second chamber, called action chamber 31. The sucking passage 27 and release passage 29 open into the first chamber 320. The chambers described above are provided within the depths of the upper wall of the connector 2. The membrane 351 is almost parallel to the upper surface of the collector 2 which forms the base of the cavity defined by the casing 35 and is therefore almost perpendicular to passages 27 and 29. The second chamber 340 which is located, in FIG. 5, above the first chamber 320 is connected to an air pump (not shown on FIG. 5) by a connection tube 319.

Figure 5:
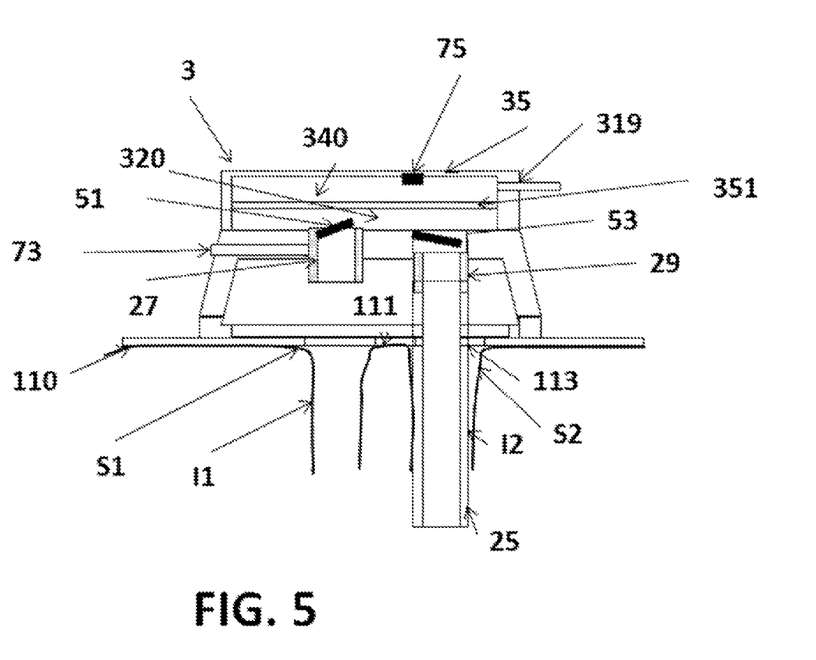
FIG. 5 represents a partial transverse section view along the longitudinal access of the intestine of part of the pump forming means and an alternative embodiment of the first and second watertight connection means according to a second embodiment of the present invention.
Figure 6:
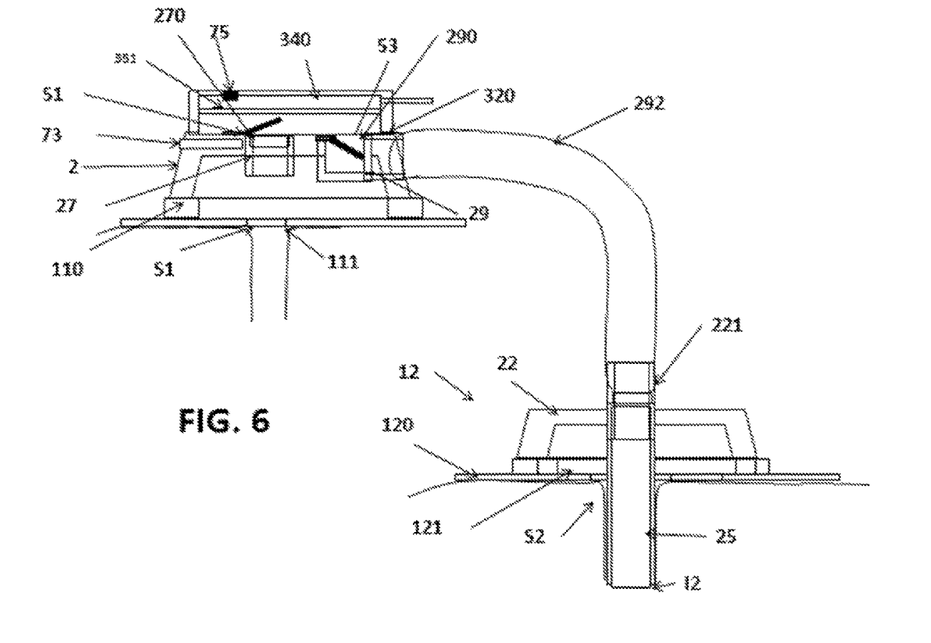
FIG. 6 represents a partial transverse section view of an alternative embodiment of the second embodiment shown in FIG. 5.

With reference to FIG. 5, the opening of the sucking passage 27 is equipped with an anti-reflux valve located in the first chamber 320 in order to avoid any food bolus reflux from the first chamber 320 towards the collector 2. Similarly the release passage 29 is equipped with an anti-reflux valve 53 in order to avoid any food bolus reflux from the exit flow tube 25 towards the first chamber 320.

With reference to FIG. 5, a temperature sensor 73 is located almost inside the sucking passage 27. This temperature sensor 73 can detect temperature variations inside the sucking passage 27. A greater temperature correspond to the presence of food bolus in the sucking passage 27 or near thereto. A pressure sensor 75 is positioned in the second chamber 340 and can detect air pressure variations inside the second chamber 340. The temperature sensor 73 and pressure sensor 75 form part of the control means 5.

The control means are similar to that described for the first embodiment.

The operation of this second embodiment will be described in more detail with reference to FIGS. 4 and 5.

Firstly the device is calibrated before operation. The temperature sensor 73 measures the temperature of the air inside the sucking passage 27. This value represents the reference value for the "empty" device, i.e. not containing food bolus. Similarly, the pressure sensor 75 measures air pressure inside the second chamber 340. The pressure measured represents the reference value for the "empty" device.

Sensors 73 and 75 then regularly measure the temperature of the medium contained in the sucking passage 27 and air pressure in the second chamber 340, respectively. The time period between two temperature and pressure measurements is a test period which is adjustable by the user through control means (for example the Bluetooth® tablet). When food bolus leaves through the upstream stoma S1 because of contractions of the upstream portion of the intestine I1, food bolus enters the collector 2 and reaches the section of the sucking passage 27 located near the temperature sensor 73. Food bolus then fills the first chamber 320 until it exerts pressure which deforms the membrane 351. Sensors 73 and 75 continue to perform their respective measurements. One of these measurements is taken when food bolus fills the sucking passage 27 and enters the first chamber 320, thereby deforming the membrane 351. Sensor 73 measures the temperature, compares it with said reference value and detects the presence of food bolus. The pressure sensor 75 is a safety feature. It only measures the variation in pressure in the second chamber when the membrane 351 bulges correctly towards the inside of the second chamber 340 as evidence that the first chamber is becoming increasingly full with food bolus. When the sensor 75 detects a pressure increase over a given threshold in the second chamber and the temperature sensor 73 has measured a temperature increase, the control means then activate the pump forming means 3. The air pump 318 injects air into the second chamber, 340 which results in bulging of the membrane 351 towards the interior of the first chamber 320. The internal volume of this chamber is then reduced and food bolus contained therein closes the anti-reflux valve 51 and passes through the release passage 29 and the exit flow tube 25. Food bolus is therefore ejected into the downstream portion of the intestine I2. The air pump 318 then sucks the air contained in the second chamber 340 which bulges the membrane 351 towards the interior of the second chamber 340. The volume of the first chamber 320 increases with the effect that food bolus contained in the collector 2 is pumped through the sucking 27. The deformation cycles for the membrane 351 continue until the temperature sensor no longer detects the presence of food bolus, i.e. until it detects a fall in temperature. The cycles may also be performed over a given programmable period using the control means.

An alternative embodiment will now be described with reference to FIG. 6. The parts in common with the second embodiment are referenced identically. FIG. 6 represents stomas S1 and S2 which are distant from each other. In this case, the first watertight connection means 11 comprise a collector 2 assembled on top of a membrane pump contained within the casing 35. The difference with the embodiment shown in FIG. 5 is that the release passage 29 crosses the wall of the collector 2 and is extended by a flexible connection tube 292. This connection tube 292 is connected to a second collector 22 which equips the second watertight connection means 12. The second watertight connection means 12 comprise a base 120 which is identical to the base 110 onto which the collector 22 is assembled. The collector 22 comprises a rigid tubing 221 onto the end of which a connection tube 292 is assembled. The rigid tubing 221 has a second end located in the collector 22. The exit flow tube 25 is assembled onto this second end of the tubing 221 within the collector 22 and therefore extends the connection tube 292. The exit flow tube 25 crosses a passage 121 provided within the base 120 and located next to the downstream stoma S2 in order to enter portion I2 of the intestine through the downstream stoma S2.

According to an alternative which is not shown, the membrane pump comprises a membrane which is locally deformed by mechanical fingers located in a second chamber of the casing. There are three of these mechanical fingers. One finger is positioned in the second chamber above the opening through which the sucking passage opens. A second finger is located in the second chamber near to the opening of the release passage. A third finger is located between the two other fingers. The fingers may be close to or distant from the membrane. They may touch the membrane and produce elastic deformation. This alternative operates as follows: in order to suck food bolus contained in the connector, the second finger is activated in order to press the membrane against the opening through which the exit flow passage opens in order to block food bolus entering the first chamber. The second finger is activated to close the entry circuit and the third finger is then activated to press the membrane in order to push food bolus contained in the first chamber towards the release passage. At the same time, the second finger is distanced from the release passage in order to allow food bolus passing through. The aforementioned fingers replaced the air pump and act both as an anti-reflux valve and the pump forming means.

What is claimed is:

1. A device enabling food bolus flow between an upstream stoma and a downstream stoma, said device comprising a pump having an entry opening and an exit opening, said pump configured for sucking a food bolus through said entry opening and releasing it through said exit opening, wherein said device further comprises:
   a first base onto which a food bolus collector is mounted, said first base having a first surface adapted for being fixed in a watertight manner to skin of a patient's abdomen, said base further having a second surface comprising said food bolus collector and at least one passage provided within said first base and opening into said food bolus collector;
   a second base onto which the food bolus collector is mounted, said second base having a first surface adapted for being fixed in a watertight manner to the patient's skin, said second base further having a second surface comprising said food bolus collector and at least one passage provided within said second base and opening into said food bolus collector;
   said pump being able to be activated by a user from the outside of said patient's body and suitable for being mounted on the patient's abdomen, in such a manner that once said device is mounted onto said patient's abdomen, food bolus flow can circulate from said upstream stoma to said downstream stoma outside of said patient's body.

2. The device according to claim 1, wherein said second base comprises an exit flow tube connected to said exit opening and configured to be introduced into a patient's intestine through said downstream stoma.

3. The device according to claim 1, wherein said pump comprises at least one deformable part and an arm for deforming said deformable part, said deformable part defining at least partially a space communicating with said first base through said entry opening and communicating with said second base through said exit opening, wherein deformation of said deformable part changes the volume of said space, for causing said volume of said space to be reduced and said food bolus inside said space to be expressed into said second base, and when the volume of said space increases, food bolus coming from said first base is sucked into said space.

4. The device according to claim 3, wherein said deformable part comprises a membrane and said pump comprises a casing, an internal space of said casing being divided into a first and second chamber by said membrane, said first chamber communicating with said first base and said second base, said pump further comprising a sucking channel, connected to said second chamber and capable of varying the pressure of said fluid within said second chamber, with the result of varying the curve of said deformable membrane, therefore enabling the volume of the first chamber to change and said food bolus to be sucked into said first chamber or released from said first chamber.

5. The device according to claim 1, wherein said device further comprises a first antireflux valve provided for avoiding reflux of said food bolus sucked by said pump towards said first base and/or second valve forming means configured for avoiding reflux of said food bolus released by said pump forming means towards said second base.

6. The device according to claim 1, wherein said device further comprises a microcontroller for controlling said pump, said microcontroller comprising an internal real time clock configured for activating said pump after a given rest period and for programming said real time internal clock therethrough once said rest period is selected.

7. The device according to claim 6, wherein said device further comprises
   sensors for detecting the presence of said food bolus downstream to said first base and/or upstream to said second base, said sensors configured to measure a parameter depending on food bolus presence or absence and to activate said pump once the value of said parameter corresponds to the presence of said food bolus inside said device;
   a safety trigger, which activates said sensors after a test period selected by the user; and which
   adjusts said test period.

8. The device according to claim 7, wherein said sensors comprise at least one sensor selected from capacitive sensors, optical sensors, temperature sensors and pressure sensors.

9. A method for circulating food bolus between an upstream stoma and a downstream stoma, both stomas being located on a patient's abdomen, wherein comprising sucking food bolus contained in the patient's intestine linked to said upstream stoma upstream to said upstream stoma and then releasing said bolus into said patient's intestine downstream to said downstream stoma and through said downstream stoma.

10. The method according to claim 9, further comprising detecting a presence of said food bolus is detected in said upstream stoma or between said upstream stoma and said downstream stoma before said sucking of said food bolus contained in the intestine upstream to said upstream stoma.

11. The device according to claim 1, wherein said pump is mounted on said patient's abdomen.

12. A device enabling food bolus flow between an upstream stoma and a downstream stoma, said device comprising a pump having an entry opening and an exit opening, said pump configured for sucking a food bolus through said entry opening and releasing it through said exit opening, wherein said device further comprises,
   a common base onto which a food bolus collector is mounted, said common base having a first surface adapted for being fixed in a watertight manner to skin of a patient's abdomen, said common base further having a second surface comprising said food bolus collector and at least one passage provided within said common base and opening into said food bolus collector,
   said pump being able to be activated by a user from outside of said patient's body and suitable for mounting onto said patient's abdomen, in such a manner that once said device is mounted onto said patient's abdomen, food bolus flow can circulate from the upstream stoma to the downstream stoma outside of said patient's body.

13. The device according to claim 12, wherein said common base comprises an exit flow tube connected to said exit opening and configured to be introduced into the patient's intestine through said downstream stoma.

14. The device according to claim 12, wherein said pump comprises at least one deformable part and an arm for deforming said deformable part, said deformable part defining at least partially a space communicating with said common base through said entry opening and communicating with said common base through said exit opening, wherein deformation of said deformable part changes the volume of said space, for causing said volume of said space to be reduced and said food bolus inside said space to be expressed into said exit opening, and when the volume of said space is increased, food bolus coming from said common base is sucked into said space.

15. The device according to claim 14, wherein said deformable part comprises a membrane and said pump comprises a casing, an internal space of said casing being divided into a first and a second chamber by said membrane, said first chamber communicating with said common base, said pump further comprising a sucking channel connected to said second chamber and capable of varying the pressure of said fluid within said second chamber, with the result of varying a curve of said deformable membrane and thereby enabling the volume of the first chamber to change and said food bolus to be sucked into said first chamber or released from said first chamber.

16. The device according to claim 12, wherein said device further comprises a first antireflux valve for avoiding reflux of said food bolus sucked by said pump towards said common base, and/or a second valve configured for avoiding reflux of said food bolus released by said pump-forming means toward said common base.

17. The device according to claim 12, wherein said device further comprises a microcontroller for controlling said pump, said microcontroller comprising an internal real time clock configured for activating said pump after a given rest period and a programmer for programming said real time internal clock therethrough once said rest period is selected.

18. The device according to claim 17, wherein said device further comprises:
   sensors for detecting the presence of said food bolus downstream to said common base and/or upstream to said common base, said sensors configured to measure a parameter depending on food bolus presence or absence and to activate the pump once the value of said parameter corresponds to the presence of said food bolus inside said device; and
   a safety trigger which activates said sensors after a test period selected by the user, and which adjusts the test period.

* * * * *